United States Patent
Miller (10) Patent No.: US 9,132,264 B2
(45) Date of Patent: Sep. 15, 2015

(54) DEPLOYABLE AND RETRACTABLE MEMBER FOR INJECTION PORT

(75) Inventor: Christopher C. Miller, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 559 days.

(21) Appl. No.: 12/938,719

(22) Filed: Nov. 3, 2010

(65) Prior Publication Data

US 2012/0108893 A1    May 3, 2012

(51) Int. Cl.
*A61M 39/02* (2006.01)
*A61M 39/04* (2006.01)
*A61F 5/00* (2006.01)

(52) U.S. Cl.
CPC .......... *A61M 39/0208* (2013.01); *A61F 5/0056* (2013.01)

(58) Field of Classification Search
CPC ............ A61M 39/0208; A61M 39/04; A61M 5/14276; A61M 5/14586; A61M 2039/0205; A61M 2039/0208; A61M 2039/0211; A61M 2039/0214; A61M 2039/0238
USPC ................................ 600/37; 604/288.01, 175
See application file for complete search history.

(56) References Cited

U.S. PATENT DOCUMENTS

| 6,067,991 | A  | 5/2000  | Forsell |
| 6,461,292 | B1 | 10/2002 | Forsell |
| 6,470,892 | B1 | 10/2002 | Forsell |
| 7,351,240 | B2 | 4/2008  | Hassler, Jr. et al. |
| 7,390,294 | B2 | 6/2008  | Hassler, Jr. |
| 7,416,528 | B2 | 8/2008  | Crawford et al. |
| 7,442,165 | B2 | 10/2008 | Forsell |
| 7,599,744 | B2 | 10/2009 | Giordano et al. |
| 7,621,863 | B2 | 11/2009 | Forsell |
| 7,699,770 | B2 | 4/2010  | Hassler, Jr. et al. |
| 7,775,215 | B2 | 8/2010  | Hassler, Jr. et al. |

(Continued)

FOREIGN PATENT DOCUMENTS

| EP | 2 070 494  | 6/2009 |
| WO | WO 01/21251 | 3/2001 |

OTHER PUBLICATIONS

U.S. Appl. No. 12/640,048, filed Dec. 17, 2009, Woodruff et al.

(Continued)

*Primary Examiner* — Charles A Marmor, II
*Assistant Examiner* — Thaddeus Cox
(74) *Attorney, Agent, or Firm* — Frost Brown Todd LLC (57) ABSTRACT

An apparatus comprises a housing and one or more deployable protrusions. The apparatus defines a fluid reservoir and presents an upper surface. The housing is sized and configured to be implanted within a patient. The protrusions are selectively movable from a first position to a second position. The protrusions are at least partially retracted relative to the housing when the protrusions are in the first position. The protrusions are at least partially extended relative to the housing when the protrusions are in the second position. The protrusions may be in the form of substantially cylindraceous posts, semi-circular members, or other shapes. The protrusions may be actuated mechanically, electromechanically, or otherwise. The apparatus may be provided as an injection port, as part of a gastric band system or otherwise. The deployed protrusions may facilitate location of the implanted port through external palpation of the patient's abdomen.

18 Claims, 5 Drawing Sheets

(56) References Cited

U.S. PATENT DOCUMENTS

| | | |
|---|---|---|
| 7,850,660 B2 | 12/2010 | Uth et al. |
| 2006/0069436 A1* | 3/2006 | Sutton et al. ............... 623/17.13 |
| 2006/0199997 A1 | 9/2006 | Hassler, Jr. et al. |
| 2006/0224129 A1* | 10/2006 | Beasley et al. ........... 604/288.01 |
| 2006/0247584 A1 | 11/2006 | Sheetz et al. |
| 2007/0078391 A1 | 4/2007 | Wortley et al. |
| 2007/0255236 A1* | 11/2007 | Christenson et al. .... 604/288.01 |
| 2007/0270961 A1* | 11/2007 | Ferguson ................... 623/17.11 |
| 2009/0088704 A1* | 4/2009 | Chelak ..................... 604/288.04 |
| 2009/0156928 A1* | 6/2009 | Evans et al. .................... 600/424 |
| 2011/0144531 A1* | 6/2011 | Marcotte et al. .............. 600/561 |

OTHER PUBLICATIONS

International Search Report dated Mar. 19, 2012 for Application No. PCT/US2011/058744.

* cited by examiner

DEPLOYABLE AND RETRACTABLE MEMBER FOR INJECTION PORT

BACKGROUND

A variety of systems and devices have been made and used for treating morbid obesity. Some such systems and devices include adjustable gastric band systems, which are operable to restrict the flow of food from the esophagus into the stomach. Some gastric bands include a fluid-filled elastomeric bladder with fixed endpoints that encircles the stomach just inferior to the gastro-esophageal junction. When fluid is added to the bladder, the band expands against the stomach, creating a food intake restriction or stoma in the stomach. To decrease this restriction, fluid is removed from the bladder. Examples of gastric bands are disclosed in U.S. Pat. No. 7,416,528, entitled "Latching Device for Gastric Band," issued Aug. 26, 2008, the disclosure of which is incorporated by reference herein. Another example of such an adjustable gastric band is disclosed in U.S. Pat. No. 6,067,991, entitled "Mechanical Food Intake Restriction Device," issued May 30, 2000, the disclosure of which is incorporated by reference herein.

To the extent that an adjustable gastric band system includes an injection port configured to receive the needle of a syringe assembly to add or withdraw fluid to or from the gastric band, those of ordinary skill in the art will appreciate that it may be desirable in some settings to locate both the injection port and, more specifically, the center of the injection port (e.g., when the septum of the injection port is at the center of the injection port). Locating the approximate center of the injection port with some degree of accuracy may facilitate addition or withdrawal of fluid via the injection port to adjust the gastric band system. One example of a system and method for identifying the location of an injection port is disclosed in U.S. Pub. No. 2006/0211914, entitled "System and Method for Determining Implanted Device Positioning and Obtaining Pressure Data" published Sep. 21, 2006, and issued Aug. 17, 2010 as U.S. Pat. No. 7,775,215, the disclosure of which is incorporated by reference herein.

Those of ordinary skill in the art will appreciate that it may be advantageous in certain circumstances to sense pressure, strain, and/or other parameters associated with operation of a gastric band device. In some settings, it may be desirable to obtain data indicative of the pressure of fluid in a gastric band. Various examples of methods and devices for obtaining pressure data and other types of data are disclosed in U.S. Pub. No. 2006/0189888, entitled "Device for Non-Invasive Measurement of Fluid Pressure in an Adjustable Restriction Device," published Aug. 24, 2006, and issued Apr. 20, 2010 as U.S. Pat. No. 7,699,770, the disclosure of which is incorporated by reference herein. Additional examples of methods and devices for obtaining pressure data and other types of data are disclosed in U.S. Pub. No. 2006/0199997, entitled "Monitoring of a Food Intake Restriction Device," published Sep. 7, 2006, and issued Sep. 13, 2011 as U.S. Pat. No. 8,016,745, the disclosure of which is incorporated by reference herein. Such parameter data may be obtained before, during, and/or after adjustment of a gastric band, and may be useful for adjustment, diagnostic, monitoring, or other purposes, and may also be obtained with respect to a mechanically actuated gastric band. In settings where a fluid-filled gastric band is used, pressure data may be used to determine whether the amount of fluid in the gastric band needs to be adjusted; and/or for other purposes.

While a variety of gastric band systems have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

FIGS. 1-4 illustrate an exemplary gastric band system (10). As shown, gastric band system (10) comprises an injection port (12), a gastric band (20), and a catheter (18). Injection port (12) of the present example comprises a port housing (14) and a needle penetrable septum (16). Port housing (14) defines a fluid reservoir (not shown) beneath septum (16), such that a needle may pierce septum (16) to reach the reservoir and add or withdraw fluid (e.g., saline, etc.) as described in greater detail below. Port housing (14) may be formed of titanium, plastic, or any other suitable material or combination of materials. Septum (16) may be formed of silicone or any other suitable material or combination of materials. Injection port (12) may be subcutaneously secured over a patient's sternum, to the patient's abdominal fascia, or in any other suitable location. In some versions, injection port (12) is configured and operable in accordance with the teachings of U.S. Pub. No. 2005/0283118, entitled "Implantable Medical Device with Simultaneous Attachment Mechanism and Method," published Dec. 22, 2005, and issued Dec. 14, 2010 as U.S. Pat. No. 7,850, 660, the disclosure of which is incorporated by reference herein. Alternatively, injection port (12) may have any other suitable configuration and/or operability.

Figure 1:
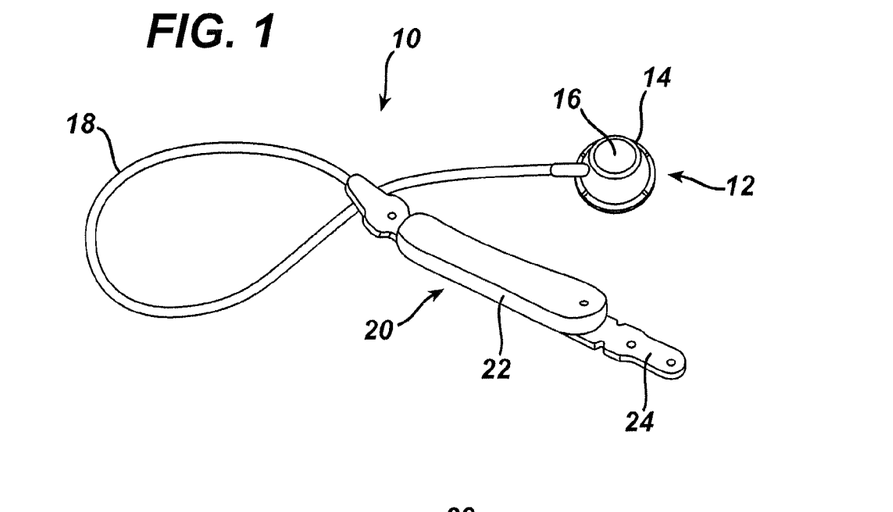
FIG. 1 depicts a perspective view of an implantable portion of an exemplary gastric band system.

Gastric band (20) of the present example comprises an inflatable bladder (22) that is secured to a flexible strap (24). Inflatable bladder (22) may be formed of silicone or any other suitable material or combination of materials. Catheter (18) provides fluid communication between bladder (22) and the reservoir of injection port (12). In the present example, catheter (18), bladder (22), and injection port (12) form a closed fluid circuit. Accordingly, a needle that is inserted through septum (16) may be used to add or withdraw fluid from inflatable bladder (22), to adjust the restriction created by gastric band (20) as described in greater detail below. In some versions, gastric band (20) is configured and operable in accordance with the teachings of U.S. Pat. No. 7,416,528, entitled "Latching Device for Gastric Band," issued Aug. 26, 2008, the disclosure of which is incorporated by reference herein. Alternatively, gastric band (20) may have any other suitable configuration and/or operability.

Figure 2:
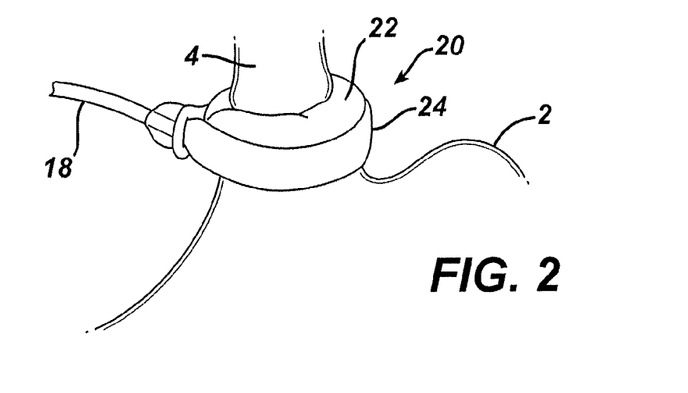
FIG. 2 depicts a perspective view of the gastric band of FIG. 1, showing the band positioned around the gastro-esophageal junction of a patient.

In some settings, gastric band (20) is applied about the gastro-esophageal junction of a patient. In particular, and as shown in FIG. 2, gastric band (20) is installed such that bladder (22) is adjacent to the tissue of the gastro-esophageal junction, with strap (24) on the outside of bladder (22). The ends of strap (24) are secured relative to each other when gastric band (20) is sufficiently wrapped about the patient's stomach (2). While strap (24) is flexible in this example, strap (24) substantially resists stretching along its length. Accordingly, when fluid is added to bladder (22) (e.g., using a needle inserted through septum (16) of injection port (12), etc.), bladder (22) expands and exerts inward forces on the gastroesophageal junction of the patient. This reduces the size of the internal stoma at the gastro-esophageal junction, thereby creating a restriction on food intake into the patient's stomach (2). It should be understood that the size of this stoma may be decreased by adding more fluid to bladder (22) to create a greater degree of restriction; or increased by withdrawing fluid from bladder (22) to reduce the degree of restriction.

Figure 3:
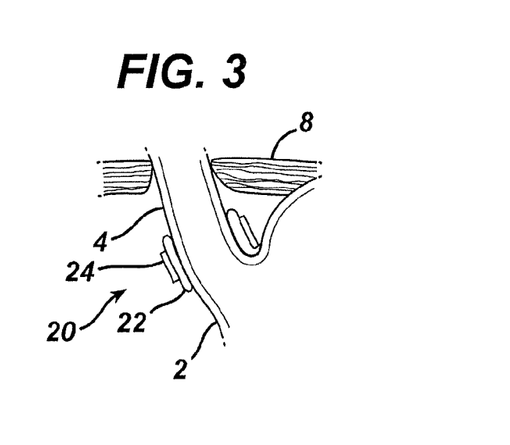
FIG. 3 depicts a cross-sectional view of the gastric band of FIG. 1, showing the band positioned around the gastro-esophageal junction of a patient in a deflated configuration.
Figure 4:
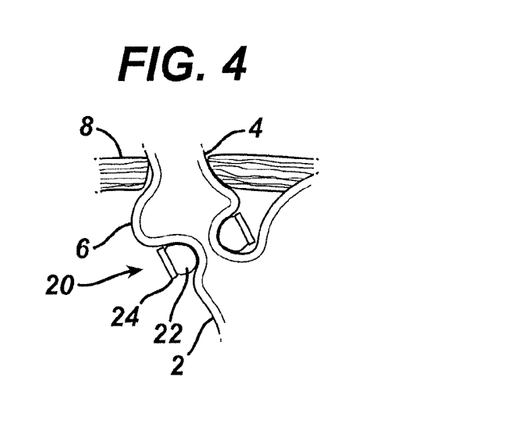
FIG. 4 depicts a cross-sectional view of the gastric band of FIG. 1, showing the band positioned around the gastro-esophageal junction of a patient in an inflated configuration to create a food intake restriction.

As shown in FIGS. 2-4, an installed gastric band (20) at least substantially encloses the upper portion of stomach (2) near the junction with esophagus (4) in the present example. FIG. 3 shows gastric band (20) in a deflated configuration, where bladder (22) contains little to no fluid, thereby maximizing the size of the stoma opening into stomach (2). FIG. 4 shows gastric band (20) in an inflated, fluid-filled configuration, where bladder (22) contains substantially more fluid than is shown in FIG. 3. In this configuration shown in FIG. 4, the pressure of gastric band (20) against stomach (2) is increased due to the fluid within bladder (22), thereby decreasing the stoma opening to create a food intake restriction. FIG. 4 also schematically illustrates the dilation of esophagus (4) above gastric band (20) to form an upper pouch (6) beneath the diaphragm muscle (8) of the patient.

In some versions, it may be necessary or desired to locate port (12) after gastric band system (10) has been installed in a patient. For instance, it may be necessary or desired to locate port (12) in order to insert a needle into septum (16) to add fluid to or withdraw fluid from gastric band system (10). As an example, this may be done in order to adjust the amount of fluid in gastric band system (10) in response to weight loss by the patient in whom gastric band system (10) is implanted or for other purposes. As another merely illustrative example, it may be necessary or desired to locate port (12) in order to perform transcutaneous energy transfer (TET) and/or telemetry communication with port (12) with an antenna/transceiver that is external to the patient. With port (12) being fully implanted in the patient, the physician or clinician may palpate the patient's abdomen until the physician or clinician can generally feel port (12) through the patient's skin and underlying tissue. In instances where palpation is used to locate port (12), it may assist the process of finding the port through palpation if port (12) has one or more structural features that can be recognized by the palpating physician or clinician. To that end, port (12) may include one or more portions that are selectively extended to help make port (12) "stand out" during palpatory location; and that are selectively retracted during other times. Various examples of how a port (12) may include such selectively extendable/retractable portions are described in greater detail below, while other examples will be apparent to those of ordinary skill in the art in view of the teachings herein. It should also be understood that a port (12) may include selectively extendable/retractable portions for a variety of other purposes, in addition to or in lieu of including such features to assist in location of port (12) by palpation.

Figure 5:
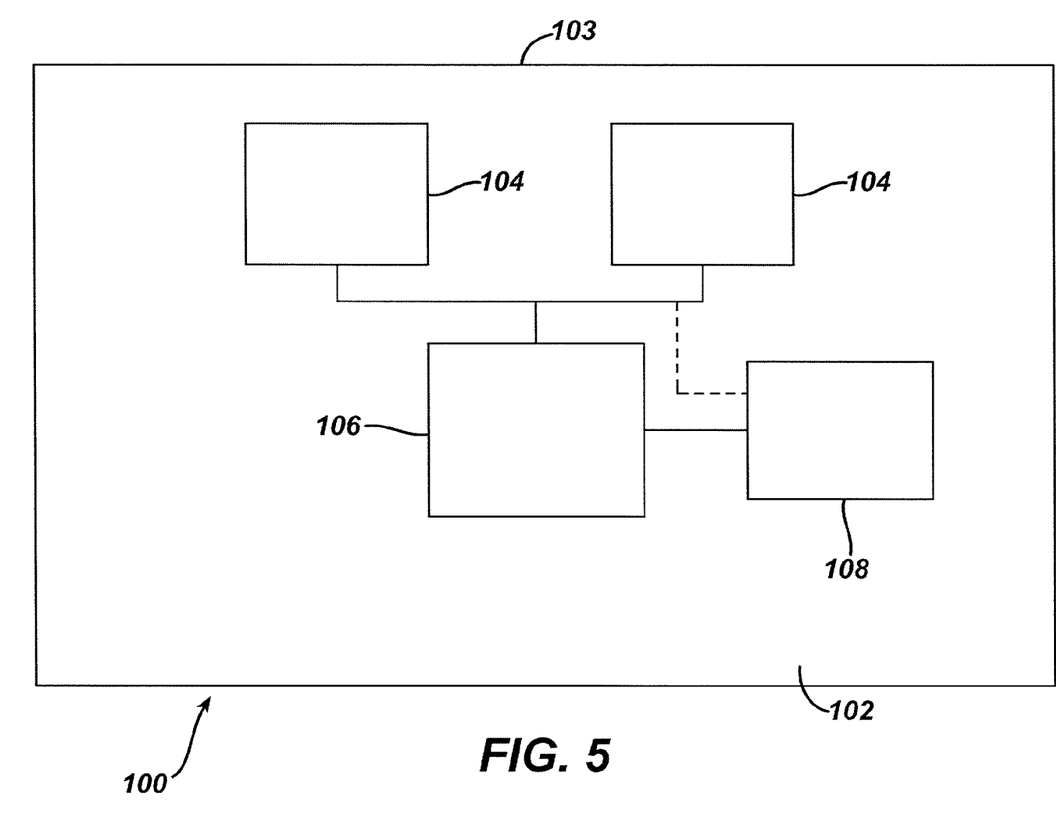
FIG. 5 depicts a diagrammatic view of an exemplary injection port with mechanically actuated retractable protrusions, which may be used with the gastric band of FIG. 1.

FIG. 5 illustrates an exemplary injection port (100) that may be used in gastric band system (10), as a substitute for the relatively simpler injection port (12) shown in FIG. 1. FIG. 5 shows various mechanical components of injection port (100) in diagram form. Port (100) of this example includes a pair of retractable protrusions (104), an actuator (106), and a trigger (108). Protrusions (104) are operable to selectively retract into body (102) of port (100). For instance, when protrusions (104) are retracted into port body (102), the tops of protrusions (104) may be substantially flush with or recessed relative to the top surface (103) of port body (102). Protrusions (104) may also be selectively extended from port body (102), such that protrusions (104) protrude above top surface (103) of port body (102). Various forms that protrusions (104) may take will be described in greater detail below with reference to FIGS. 7A-7B and 8A-8B, while other forms that protrusions (104) may take will be apparent to those of ordinary skill in the art in view of the teachings herein. It should also be understood that, while FIG. 5 depicts two protrusions (104), port (100) may instead include any other suitable number of protrusions (104).

Actuator (106) may include a variety of components, features, and configurations. For instance, in some versions, actuator (106) includes one or more springs or other types of resilient members and/or one or more other types of components that store mechanical energy. Such a spring or other type of resilient member may be configured to bias protrusions (104) to an extended position. In addition or in the alternative, one or more springs or other types of resilient members may be configured to bias protrusions (104) to a retracted position. It should also be understood that actuator (106) may selectively transition protrusions (104) from a retracted position to an extended position by simply translating protrusions (104) along respective linear paths, by rotating protrusions (104) along respective curved paths, by rotating protrusions (104) about a point or axis (e.g., at a hinge, etc.), and/or in any other suitable fashion.

As yet another merely illustrative variation, actuator (106) may provide actuation of protrusions (104) by pressure from a stored fluid (e.g., a stored gas or liquid, etc.). Such a fluid may be stored in a pressure vessel that is integral with injection port (100) and/or a pressure vessel that is separate from but coupled with injection port (100). Pressurized fluid may be selectively communicated from such a vessel to actuator (106) and/or directly to protrusions (104) by a valve or regulator positioned along a fluid path between such components. Such a valve or regulator may be coupled with trigger (108) such that the valve or regulator is configured to provide a predefined amount of fluid (e.g., just enough to actuate protrusions (104), etc.) in response to external palpation of the patient's abdomen in a region above injection port (100). Various ways in such a valve or regulator may be configured will be apparent to those of ordinary skill in the art in view of the teachings herein. It should also be understood that pressure gradients created by a stored fluid may be used to actuate protrusions (104) and/or to retract protrusions (104) after protrusions (104) have been actuated. For instance, fluid may be injected or removed from a pressure vessel via a septum to create such pressure gradients.

In the present example, each protrusion (104) is actuated by the same actuator (106), though it should be understood that each protrusion (104) may alternatively be associated with its own respective actuator (106) and/or various other suitable relationships may be used. Various suitable components, features, and configurations that may be incorporated into actuator (106) and/or may be otherwise associated with actuator (106) will be apparent to those of ordinary skill in the art in view of the teachings herein.

Trigger (108) is configured to selectively activate actuator (106). Like actuator (106), trigger (108) may include a variety of components, features, and configurations. For instance, trigger (108) may include a part of port (100) that is movable relative to port body (102), and may include a pawl or other feature that provides a trip mechanism for actuator (106). In some versions, protrusions (104) are directly coupled with trigger (108), in addition to being coupled with trigger (108) indirectly through actuator (106). For instance, even when protrusions (104) are in a retracted position, protrusions (104) may be moved slightly downward by a physician or clinician palpating a patient's abdomen or other area associated with implantation of port (100). Such downward movement of protrusions (104) may move at least part of trigger (108), which may in turn activate actuator (106), which may in turn deploy protrusions (104) from the retracted position to the extended position.

It should be understood from the foregoing that trigger (108) of the present example is responsive to a physician or clinician palpating the patient's abdomen or other area associated with the implantation of port (100). As the physician or clinician generally palpates the patient's abdomen, and as the physician or clinician moves their palpating hand along the patient's abdomen, their hand is eventually located over port (100). At this stage, the palpation at this location causes trigger (108) to activate actuator (106), which in turn deploys protrusions (104) from a retracted position to an extended position. In the event that the physician or clinician does not feel protrusions (104) popping up, the physician or clinician may eventually detect protrusions (104) through tactile feedback as the physician or clinician continues to move their palpating hand along the patient's abdomen. By detecting protrusions (104) through palpation, the physician or clinician has thereby located port (100), such that the physician or clinician may then insert a needle into the septum of port (100) to add fluid to or withdraw fluid from the gastric band system. Various suitable components, features, and configurations that may be incorporated into trigger (108) and/or may be otherwise associated with trigger (108) will be apparent to those of ordinary skill in the art in view of the teachings herein.

In some settings, trigger (108) may occasionally be pressed down (or be otherwise activated) by the patient's own movements or positioning. It may be desirable to prevent such incidental pressing of trigger (108) from causing deployment of protrusions (104) by actuator (106). To that end, trigger (108) may be configured such that a certain amount of force must be exerted on trigger (108) in order for trigger to activate actuator (106). The predetermined force threshold may be selected such that incidental pressing on trigger (108) by patient movement/positioning falls below the threshold; while sufficient external palpation by a physician exceeds the threshold. Still other suitable ways in which port (100) may prevent deployment of protrusions (104) in response to inadvertent pressing of trigger (108) will be apparent to those of ordinary skill in the art in view of the teachings herein. Of course, some versions of port (100) may lack such prevention; and some other versions of port (100) may lack a feature permitting trigger (108) to be pressed in relative to other portions of port (100).

Similarly, in some settings, it may be desirable to maintain actuator (106) and/or trigger (108) in a deactivated state until port (100) has been implanted in the patient. In other words, it may be desirable in some settings to prevent actuator (106) from deploying protrusions (104) before and during the process of installing port (100) in the patient. Otherwise, pressing of trigger (108) during the process of installing port (100) in the patient might activate actuator (106) and thereby cause inadvertent deployment of protrusions (104). There are a variety of ways in which actuator (106) and/or trigger (108) may be disabled before installation of port (100) is complete. For instance, one or more bosses or other types of mechanical lockout feature may trigger (108) from being moved downwardly toward port body (102) until after the surgeon installing port (100) has unlocked, removed, or otherwise manipulated the lockout feature. Still other suitable ways in which actuator (106) and/or trigger (108) may be selectively enabled for deployment of protrusions (104) will be apparent to those of ordinary skill in the art in view of the teachings herein.

In some versions, trigger (108) is responsive to a magnetic field in addition to or in lieu of being responsive to forces manually exerted by a physician who is palpating the patient. In other words, trigger (108) may be configured such that it activates actuator (106) to deploy protrusions (104) when a magnet having sufficient strength is passed over port (100). In some such versions, a physician may simply sweep an appropriate magnet over the patient's abdomen, chest, or other area associated with port (100), and such sweeping of the magnet may cause trigger (108) to activate actuator (106), thereby deploying protrusions (104) from a retracted position to a deployed position. The physician may then palpate the patient's abdomen, chest, or other area associated with port (100), and determine the location of port (100) by feeling deployed protrusions (104) through the patient's skin and tissue. It should also be understood that protrusions (104) and/or actuator (106) may themselves/itself be directly activated by a magnetic field provided by a magnet that is external to a patient. For instance, such an external magnet may attract one or more ferrous components of protrusions (104) and/or actuator (106), such that protrusions (104) actuate in response to the presence of the magnetic field. In some such versions, protrusions (104) are biased to a retracted position, such that protrusions (104) automatically retract once the magnetic field is taken away. Other suitable ways in which protrusions (104), actuator (106), and/or trigger (108) may be responsive to a magnetic field will be apparent to those of ordinary skill in the art in view of the teachings herein.

It should also be understood that, in some settings, it may be desirable to provide for retraction of protrusions (104) back into port body (102) after they have been deployed to the extended position while port (100) is implanted in the patient. By way of example only, port (100) may be configured such that protrusions (104) may be pressed back into port body (102) with sufficient force; and actuator (106) may be configured to retain protrusions (104) in a retracted configuration until actuator (106) is subsequently activated by trigger (108). For instance, port (100) may be configured such that palpatory forces on port (100) must exceed a first threshold before trigger (108) causes actuator (106) to deploy protrusions (104) from a retracted position to an extended position; and such that palpatory forces exerted on port (100) must exceed a second threshold (higher than the first threshold) before protrusions (104) are retracted back into port body (102) from the extended position back to the retracted position. Trigger (108) may also be configured such that it allows protrusions (104) to be selectively locked back in the retracted position upon protrusions (104) being moved from the deployed position back to the retracted position.

In versions where trigger (108) is responsive to a sufficiently strong magnetic field, protrusions (104) may be selectively returned from an extended position to a retracted position by passing a physician magnet once again over the patient's chest, abdomen, or other area associated with port (100). In addition or in the alternative, protrusions (104) may be selectively returned from an extended position to a retracted position by a physician sufficiently pressing downwardly on protrusions (104), as described above or otherwise, even in versions where a magnet is used to deploy protrusions from the retracted position to the extended position.

As another merely illustrative example, retraction of protrusions (104) back into port body (102) after they have been deployed to the extended position while port (100) is implanted in the patient may be provided by a separate trigger (not shown) that is located under the septum of port (100). For instance, port (100) may include a strike plate that is configured to prevent a needle from puncturing the bottom of port (100) after the needle is inserted in the septum to adjust the level of fluid in the gastric band system. An example of such a strike plate is disclosed in U.S. Pub. No. 2005/0283118, issued as U.S. Pat. No. 7,850,660, the disclosure of which is incorporated by reference herein. Such a strike plate may be slightly movable relative to port body (102), and a trigger may be coupled with such a strike plate, such that the trigger causes a second actuator (not shown) to retract protrusions (104) into port body (102) as soon as a needle sufficiently hits the strike plate. In configurations where the strike plate is in communication with the fluid of the gastric band system, the strike plate and/or trigger may be configured such that the second actuator is not activated by incidental changes in fluid pressure that might occur due to patient activity (e.g., eating, vomiting, sitting up from a supine position, etc.). Various suitable ways in which port (100) may provide selective retraction of deployed protrusions (104) after port (100) has been implanted in the patient will be apparent to those of ordinary skill in the art in view of the teachings herein.

Figure 6:
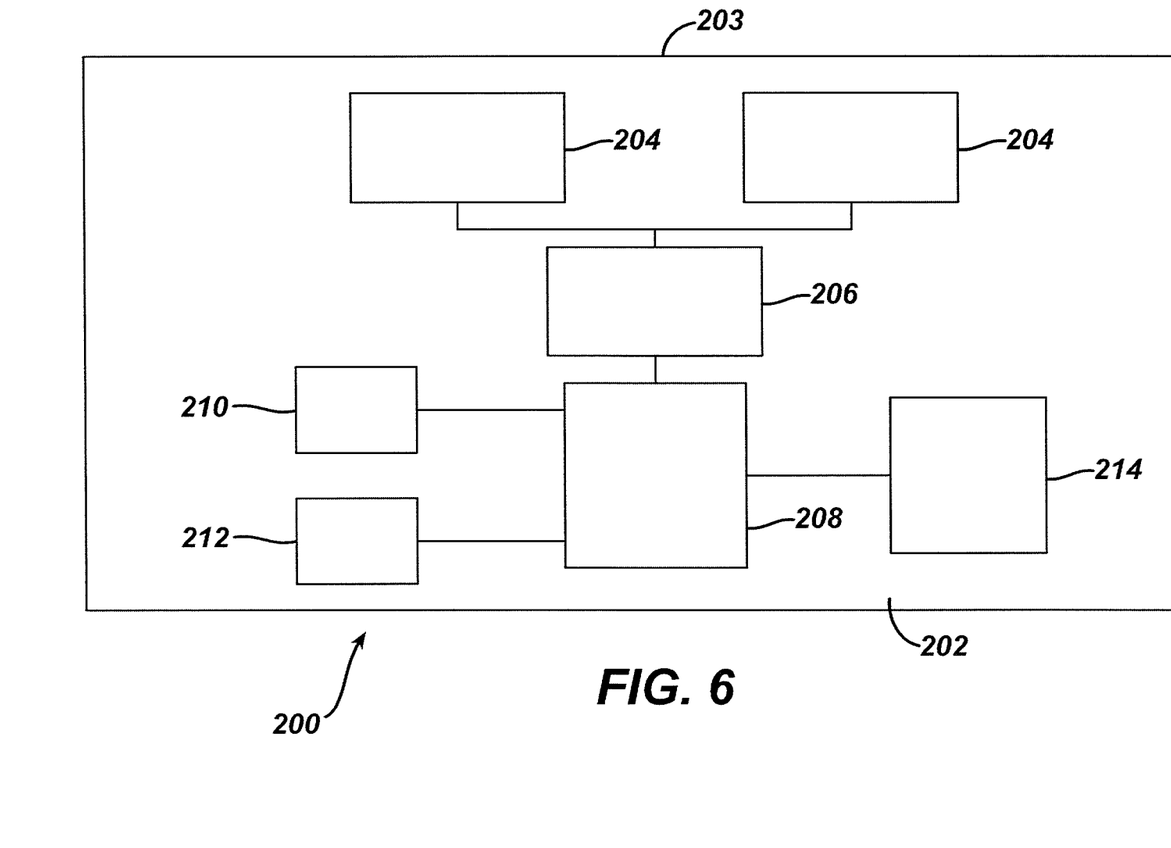
FIG. 6 depicts a diagrammatic view of an exemplary injection port with electromechanically actuated retractable protrusions, which may be used with the gastric band of FIG. 1.

FIG. 6 illustrates another exemplary injection port (200) that may be used in gastric band system (10), as a substitute for the relatively simpler injection port (12) shown in FIG. 1. FIG. 6 shows various electrical and electromechanical components of injection port (200) in diagram form. Port (200) of this example includes a pair of retractable protrusions (204), an actuator (206), a processor (208), a coil (210), an internal power source (212), and a pressure sensor (214). Protrusions (204) are operable to selectively retract into body (202) of port (200). For instance, when protrusions (204) are retracted into body (202), the tops of protrusions (204) may be substantially flush with or recessed relative to the top surface (203) of body (202). Protrusions (204) may also be selectively extended from port body (202), such that protrusions (204) protrude above top surface (203) of body (202). Various forms that protrusions (204) may take will be described in greater detail below with reference to FIGS. 7A-7B and 8A-8B, while other forms that protrusions (204) may take will be apparent to those of ordinary skill in the art in view of the teachings herein. It should also be understood that, while FIG. 6 depicts two protrusions (204), port (200) may instead include any other suitable number of protrusions (204).

Actuator (206) may include a variety of components, features, and configurations. For instance, in some versions, actuator (206) includes a solenoid that is operable to selectively transition protrusions (204) between a retracted position and an extended position by simply translating protrusions (204) along respective linear paths, by rotating protrusions (204) along respective curved paths, by rotating protrusions (204) about a point or axis (e.g., at a hinge, etc.), and/or in any other suitable fashion, in response to an electrical signal from processor (208). Actuator (206) may thus actively deploy protrusions (204) using electromechanical force. As another merely illustrative variation, actuator (206) may include a spring or other resilient member configured to bias protrusions (204) to an extended position, and actuator (206) may be operable to selectively retain protrusions (204) against the resilient bias of a spring, etc. or release protrusions (204) (in response to a signal from processor (208)) to allow spring to deploy protrusions (204). As yet another example, actuator (206) may comprise an electromechanical motor that is operable to selectively rotate protrusions (204) into deployed positions and/or to rotate one or more pinions that translate racks that are integral with protrusions (204), to move protrusions (204) along substantially linear paths. As still another example, actuator (206) may comprise an electric pump that is operable to generate pressure to selectively actuate protrusions (204). Actuator (206) may also comprise an electromagnet that is operable to selectively introduce a magnetic field to actuate protrusions (204).

In the present example, each protrusion (204) is actuated by the same actuator (206), though it should be understood that each protrusion (204) may alternatively be associated with its own respective actuator (206) and/or various other suitable relationships may be used. Various suitable components, features, and configurations that may be incorporated into actuator (206) and/or may be otherwise associated with actuator (206) will be apparent to those of ordinary skill in the art in view of the teachings herein.

In some versions, a control signal and/or power provided to actuator (206) via processor (208) at least partially originates from coil (210) of port (200). For instance, coil (210) may comprise a transcutaneous energy transfer (TET) coil that is operable to receive RF energy transcutaneously from a second coil (not shown) that is external to the patient. Such an external coil may be configured in accordance with the teachings of U.S. Pub. No. 2006/0211914, entitled "System and Method for Determining Implanted Device Positioning and Obtaining Pressure Data," published Sep. 21, 2006, and issued Aug. 17, 2010 as U.S. Pat. No. 7,775,215, the disclosure of which is incorporated by reference herein. As another merely illustrative example, such an external coil may be configured in accordance with the teachings of U.S. Pat. No. 7,599,744, entitled "Transcutaneous Energy Transfer Primary Coil with High Aspect Ferrite Core," issued Oct. 6, 2009, the disclosure of which is incorporated by reference herein. Other suitable forms that such an external coil may take will be apparent to those of ordinary skill in the art in view of the teachings herein. While the above examples include TET through RF, it should be understood that any other suitable wireless energy transfer modality may be used. It should also be understood that operational power may be provided to actuator (206) by an internal power source (212), such as a battery, etc. Furthermore, regardless of the source of power, it should be understood that actuation of protrusions (204) may be achieved without the presence of a processor (208) in port (200).

In versions where operational power is provided to actuator (206) by internal power source (212), coil (210) and processor (208) may respond to a field generated by the external coil by selectively coupling actuator (206) with power source (212) to activate actuator (206). In addition or in the alternative, the external coil and internal coil (210) may together provide operational power to vibration generator (210) via transcutaneous energy transfer (TET). Thus, a battery or other implanted power source (212) need not be included within port (200). It should be understood from the foregoing that a physician may locate port (200) by first sweeping over the patient's abdomen and/or chest with the external coil, which will ultimately cause actuator (206) to deploy protrusions (204) from a retracted position to an extended position, and then the physician may palpate the patient's abdomen or chest until they locate port (200) by feeling protrusions (204) through the patient's tissue and skin.

Yet another merely exemplary use for protrusions (204) may be to provide an alert when some condition has been detected. By way of example only, some versions of port (200) may include a pressure sensor (214) that is configured to sense the pressure of fluid in a gastric band system that includes port (200). Various suitable ways in which a pressure sensor (214) may be incorporated into a gastric band system are disclosed in U.S. Pub. No. 2006/0211914, entitled "System and Method for Determining Implanted Device Positioning and Obtaining Pressure Data," published Sep. 21, 2006, and issued Aug. 17, 2010 as U.S. Pat. No. 7,775,215, the disclosure of which is incorporated by reference herein. Alternatively, any other suitable type of pressure sensor (214) may be incorporated into the gastric band system in any suitable fashion. While FIG. 6 depicts pressure sensor (214) as a component of port (200), it should be understood that pressure sensor (214) may be located in any other suitable position or component. It should also be understood that a pressure sensor may be used in various other types of implanted devices in which the teachings herein may be incorporated. In other words, the utility of a pressure sensor in the context of at least some of the teachings herein is not limited to a gastric band system (10).

Processor (206) may be configured to monitor readings from pressure sensor (214) and compare those readings to one or more baselines. Processor (206) may further be configured to trigger deployment of protrusions (204) when a pressure data reading from pressure sensor (214) deviates from a baseline or range. For instance, processor (206) may trigger deployment of protrusions (204) by actuator (206) when the pressure of fluid in the gastric band system falls below a threshold (e.g., approximately 10 mmHg, etc.), which may indicate that there is a leak in the system, that more fluid needs to be added to the system, or some other condition. Similarly, processor (206) may trigger deployment of protrusions (204) when the pressure of fluid in the gastric band system exceeds a threshold (e.g., approximately 50 mmHg, etc.), which may indicate that fluid needs to be withdrawn from the system, or some other condition. Such pressure-based feedback may be felt by the patient (e.g., patient may feel protrusions (204) sticking into their tissue, etc.), and may prompt the patient to contact their physician for an adjustment of gastric band (200). The physician may then investigate further and provide any appropriate medical response (e.g., adding fluid to or withdrawing fluid from the gastric band system, etc.). Of course, actuator (206) may operate completely independent from pressure sensor (214) in some versions. Furthermore, pressure sensor (214) may simply be omitted from port (200) if desired. It should also be understood that pressure sensor (214) may be supplemented or replaced by one or more other sensors that are configured to sense/monitor another attribute or parameter of an implanted device or system.

As noted above, in some settings, it may be desirable to provide for retraction of protrusions (204) back into port body (202) after they have been deployed to the extended position while port (200) is implanted in the patient. For instance, actuator (206) may be configured to actively retract protrusions (204) in response to a retraction signal from processor (206). Such a retraction signal may be communicated in response to a corresponding retraction signal received by coil (210) from an external coil. In other words, an external transmitter or transceiver associated with the external coil may be operable to transmit a deployment signal to coil (210) to deploy protrusions (204) from a retracted position to an extended position; and be further operable to transmit a retraction signal to coil (210) to retract protrusions (204) from the extended position to the retracted position. In addition or in the alternative, port (200) may be configured such that protrusions (204) may be pressed back into port body (202) with sufficient force, similar to what is described above in the context of port (100). Similarly, port (200) may be configured such that protrusions (204) may be moved back from the extended position to the retracted position in any other manner described above in the context of port (100). Various other suitable ways in which port (200) may provide selective retraction of deployed protrusions (204) after port (200) has been implanted in the patient will be apparent to those of ordinary skill in the art in view of the teachings herein.

Figure 7A:
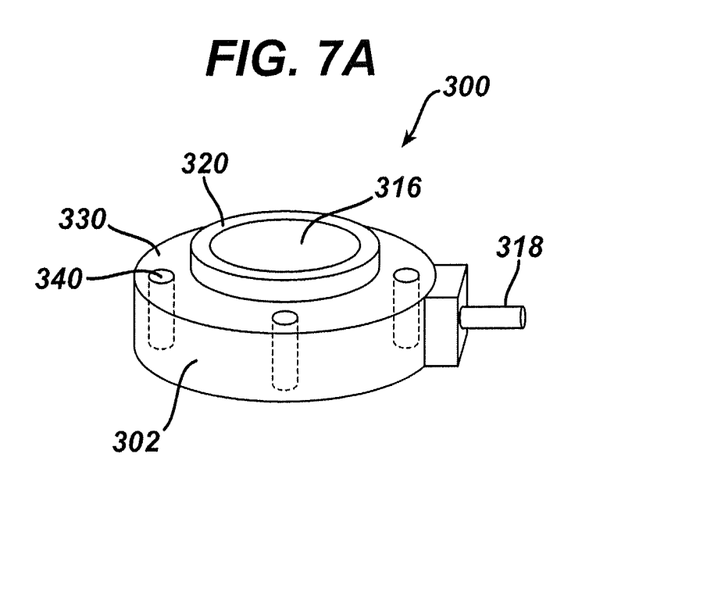
FIG. 7A depicts a perspective view of an exemplary injection port with cylindraceous retractable protrusions, with the protrusions in a retracted position.
Figure 7B:
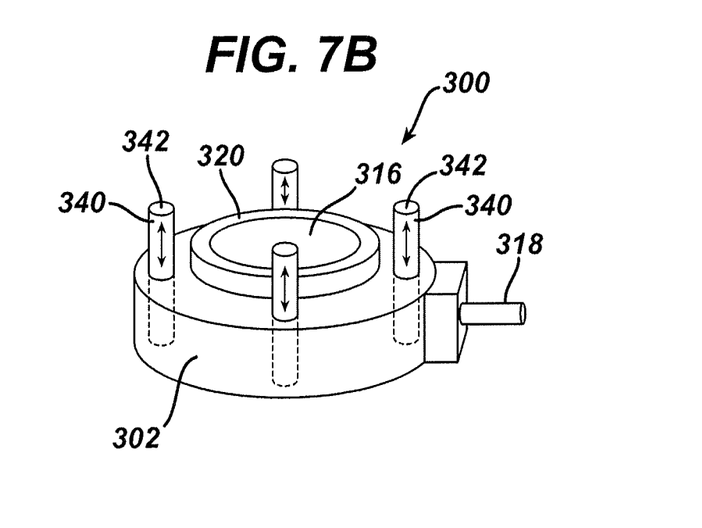
FIG. 7B depicts a perspective view of the injection port of FIG. 7A, with the protrusions in an extended position.

FIGS. 7A-7B depict a merely illustrative example of how injection ports (100, 200) of FIGS. 5-6 may be implemented. In particular, FIGS. 7A-7B show an exemplary injection port (300) that includes a port body (302), a septum (316), and selectively deployable protrusions (340). Like injection ports (12, 100, 200) described above, injection port (300) may be coupled with a gastric band (20) via a conduit, such as catheter (318) partially shown in FIGS. 7A-7B. As is also shown in FIGS. 7A-7B, protrusions (340) are movable between a retracted position, in which protrusions (340) are substantially flush with or recessed relative to the top surface (330) of port body (302) as shown in FIG. 7A, and an extended position, in which protrusions (340) extend substantially upwardly relative to top surface (330) of port body (302) as shown in FIG. 7B. Protrusions (340) may be deployed from the retracted position to the extended position by an actuator (106) as described above in the context of FIG. 5, by an actuator (206) as described above in the context of FIG. 6, or in any other suitable fashion.

In the present example, a septum retainer ring (320) is positioned above top surface (330) and around septum (316). In some versions, ring (320) is configured to slightly move relative to port body (302), linearly along an axis passing through the center of port (300). In some such versions, ring (320) acts as trigger (108) described above. In other words, with port body (302) being grounded and secured to a patient's abdominal fascia (or some other place), a physician's external palpation of the patient's abdomen (or other place) exerts force on ring (320), causing ring (320) to retract slightly relative to port body (330), thereby triggering protrusions (340) to move from the retracted position shown in FIG. 7A to the extended position shown in FIG. 7B. Of course, port (300) may be configured such that any other suitable stimulus causes deployment of protrusions (340), and ring (320) may be substantially immobile relative to port body (330) in some versions. Other suitable ways in which deployment of protrusions (340) may be triggered will be apparent to those of ordinary skill in the art in view of the teachings herein.

In the example shown in FIGS. 7A-7B, protrusions (340) are configured as posts having a substantially cylindraceous shape. The upper tips (342) of protrusions (340) are generally blunt, such that protrusions (340) do not penetrate adjacent tissue above port (300) when protrusions (340) are deployed from a retracted position to an extended position while port (300) is implanted in a patient. In addition, protrusions (340) have a height that is substantially equal to the height of port body (320) in the present example. Thus, the effective height of port (300) nearly doubles when protrusions (340) are deployed, substantially increasing the likelihood that the location of implanted port (300) may be detected through tactile feedback during manual external palpation of the patient's abdomen. Furthermore, the substantially cylindraceous shape of protrusions (340) may be readily recognizable by the palpating physician. The arrangement of protrusions (340) about septum (316) may also allow the physician to better determine the location of septum (316), which may help the physician more accurately target septum (316) with a needle. Of course, protrusions (340) may have any other suitable shape and any suitable height. For instance, the upper tips (342) may be substantially rounded instead of being substantially flat with sharp corners. It should also be understood that, instead of having one or more discrete protrusions (340), the entire upper surface (330) of port (300) may selectively extend and retract relative to port body (302). Thus, it is contemplated that protrusions (340) may have any suitable geometry. Other suitable shapes/geometries will be apparent to those of ordinary skill in the art in view of the teachings herein. Furthermore, it should be understood that protrusions (340) may be provided in any suitable number and in any other suitable arrangement.

Figure 8A:
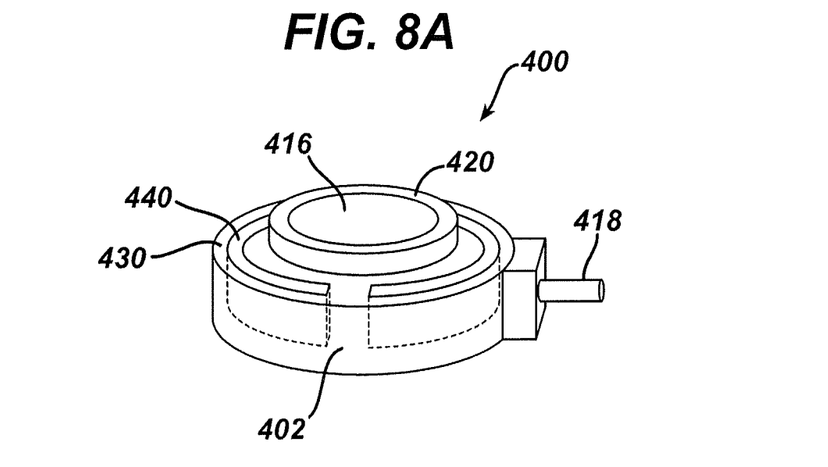
FIG. 8A depicts a perspective view of an exemplary injection port with arcuate retractable protrusions, with the protrusions in a retracted position.
Figure 8B:
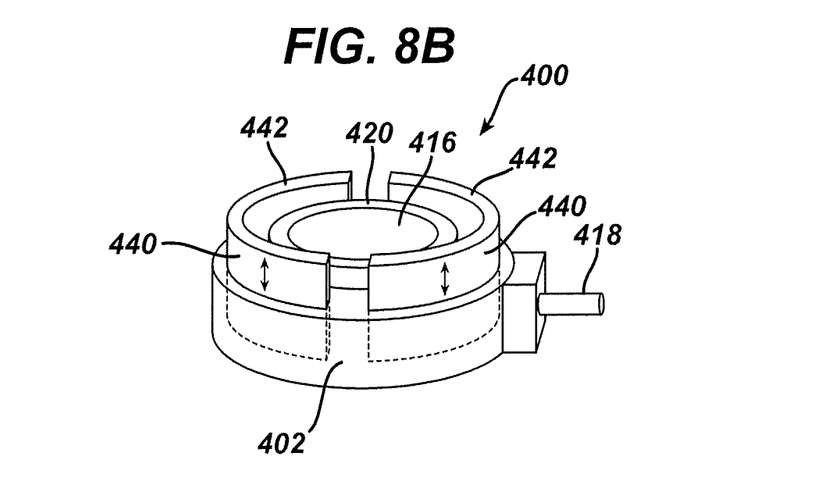
FIG. 8B depicts a perspective view of the injection port of FIG. 8A, with the protrusions in an extended position.

FIGS. 8A-8B depict another merely illustrative example of how injection ports (100, 200) of FIGS. 5-6 may be implemented. In particular, FIGS. 8A-8B show an exemplary injection port (400) that includes a port body (402), a septum (416), and selectively deployable protrusions (440). Like injection ports (12, 100, 200, 300) described above, injection port (400) may be coupled with a gastric band (20) via a conduit, such as catheter (418) partially shown in FIGS. 8A-8B. As is also shown in FIGS. 8A-8B, protrusions (440) are movable between a retracted position, in which protrusions (440) are substantially flush with or recessed relative to the top surface (430) of port body (402) as shown in FIG. 8A, and an extended position, in which protrusions (440) extend substantially upwardly relative to top surface (430) of port body (402) as shown in FIG. 8B. Protrusions (440) may be deployed from the retracted position to the extended position by an actuator (106) as described above in the context of FIG. 5, by an actuator (206) as described above in the context of FIG. 6, or in any other suitable fashion.

In the present example, a septum retainer ring (420) is positioned above top surface (430) and around septum (416). In some versions, ring (420) is configured to slightly move relative to port body (402), linearly along an axis passing through the center of port (400). In some such versions, ring (420) acts as trigger (108) described above. In other words, with port body (402) being grounded and secured to a patient's abdominal fascia (or some other place), a physician's external palpation of the patient's abdomen (or other place) exerts force on ring (420), causing ring (420) to retract slightly relative to port body (430), thereby triggering protrusions (440) to move from the retracted position shown in FIG. 8A to the extended position shown in FIG. 8B. Of course, port (400) may be configured such that any other suitable stimulus causes deployment of protrusions (440), and ring (420) may be substantially immobile relative to port body (430) in some versions. Other suitable ways in which deployment of protrusions (440) may be triggered will be apparent to those of ordinary skill in the art in view of the teachings herein.

In the example shown in FIGS. 8A-8B, protrusions (440) have a substantially arcuate, semi-circular shape. The upper surfaces (442) of protrusions (440) are generally blunt, such that protrusions (440) do not penetrate adjacent tissue above port (400) when protrusions (440) are deployed from a retracted position to an extended position while port (400) is implanted in a patient. In addition, protrusions (440) have a height that is substantially equal to the height of port body (420) in the present example. Thus, the effective height of port (400) nearly doubles when protrusions (440) are deployed, substantially increasing the likelihood that the location of implanted port (400) may be detected through tactile feedback during manual external palpation of the patient's abdomen. Furthermore, the substantially semi-circular shape of protrusions (440) may be readily recognizable by the palpating physician. The arrangement of protrusions (440) about septum (416) may also allow the physician to better determine the location of septum (416), which may help the physician more accurately target septum (416) with a needle. Of course, protrusions (440) may have any other suitable shape and any suitable height. For instance, the upper surfaces (442) may be substantially rounded instead of being substantially flat with sharp corners. Other suitable shapes will be apparent to those of ordinary skill in the art in view of the teachings herein. Furthermore, it should be understood that protrusions (440) may be provided in any suitable number and in any other suitable arrangement.

In some versions, protrusions (104, 204, 340, 440) are configured to selectively vibrate to provide haptic feedback to a physician who is palpating the patient in an area near injection port (100, 200, 300, 400). For instance, protrusions (104, 204, 340, 440) may be configured to selectively vibrate in accordance with the teachings of U.S. patent application Ser. No. 12/640,048, entitled "Implantable Port with Vibratory Feedback," filed Sep. Dec. 17, 2009, and published Jun. 23, 2011 as U.S. Pat. Pub. No. 2011/0152901, the disclosure of which is incorporated by reference herein. Similarly, protrusions (104, 204, 340, 440) may be selectively actuated in accordance with the teachings of U.S. patent application Ser. No. 12/640,048. U.S. Pat. Pub. No. 2011/0152901. It should also be understood that various other teachings of U.S. patent application Ser. No. 12/640,048 may be readily combined with the teachings herein. Various suitable ways in which the teachings of U.S. patent application Ser. No. 12/640,048 and the teachings herein may be combined will be apparent to those of ordinary skill in the art in view of the teachings herein.

As yet another example, gastric band system (10) may include an implanted pump/reservoir system (not shown) instead of including an injection port (12). Such a pump/reservoir system may be controlled to selectively vary the amount of fluid in gastric band (20). Examples of such a system are described in U.S. Pat. No. 7,390,294, entitled "Piezo Electrically Driven Bellows Infuser for Hydraulically Controlling an Adjustable Gastric Band," issued Jun. 24, 2008, the disclosure of which is incorporated by reference herein. Other examples of such a system are described in U.S. Pat. No. 7,351,240, entitled "Thermodynamically Driven Reversible Infuser Pump for Use as a Remotely Controlled Gastric Band," issued Apr. 1, 2008, the disclosure of which is incorporated by reference herein. Such systems may include an implanted coil such that they may be powered, controlled, and/or otherwise communicated with by an external coil or antenna. Accordingly, such systems may include various components shown in FIGS. 5-6 to provide deployment of protrusions (104, 204, 340, 440) to enhance tactile feedback to a physician palpating the patient in order to assist the physician in locating an implanted coil. That is, a physician may be trying to find the approximate location of the implanted coil to determine where to position the external coil, and the physician may palpate the patient until the physician locates the implanted coil through tactile feedback provided by extended protrusions (104, 204, 340, 440) that are associated with the pump/reservoir system. Upon discovering the approximate location of the pump/reservoir system through such tactile feedback, the physician may position the external coil accordingly and control the pump/reservoir system through signals emitted by the external coil.

It should be understood from the foregoing that selectively deployed protrusions (104, 204, 340, 440) may be incorporated into virtually any type of implanted device. The above described examples of gastric band systems are mere illustrations. The inventors' contemplation is not limited to components of gastric band systems. By way of example only, selectively deployed protrusions (104, 204, 340, 440) may be incorporated into an implanted drug infusion port, chemotherapy port, or any other type of implantable port that is used to deliver something to a patient (e.g., an injection, treatment, medication, etc.), to help a physician locate the implanted port through palpation of the patient. Still other types of implanted devices that may incorporate selectively deployed protrusions (104, 204, 340, 440) will be apparent to those of ordinary skill in the art in view of the teachings herein. It should also be understood that deployed protrusions (104, 204, 340, 440) may assist in determining the orientation of an implanted device through manual palpation, in addition to making it relatively easier to determine the location of an implanted device. For instance, protrusions (104, 204, 340, 440) may provide tactile feedback to indicate to a palpating physician that an implanted device is turned on its side rather than being oriented in an upright position, etc.

It will become readily apparent to those skilled in the art that examples described herein may have applicability to other types of implantable bands. For example, bands are used for the treatment of fecal incontinence. One such band is described in U.S. Pat. No. 6,461,292, entitled "Anal Incontinence Treatment with Wireless Energy Supply," issued Oct. 8, 2002, the disclosure of which is incorporated by reference herein. Bands can also be used to treat urinary incontinence. One such band is described in U.S. Pat. No. 7,621,863, entitled "Urinary Incontinence Treatment with Wireless Energy Supply," issued Nov. 24, 2009, the disclosure of which is incorporated by reference herein. Bands can also be used to treat heartburn and/or acid reflux. One such band is described in U.S. Pat. No. 6,470,892, entitled "Mechanical Heartburn and Reflux Treatment," issued Oct. 29, 2002, the disclosure of which is incorporated by reference herein. Bands can also be used to treat impotence. One such band is described in U.S. Pat. No. 7,442,165, entitled "Penile Prosthesis," issued Oct. 28, 2008, the disclosure of which is incorporated by reference herein. Various ways in which the teachings herein may be incorporated with the teachings of these patent references will be apparent to those of ordinary skill in the art.

Versions of the present invention have application in conventional endoscopic and open surgical instrumentation as well as application in robotic-assisted surgery.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus, comprising:
   (a) a housing defining a fluid reservoir, wherein the housing is sized and configured to be implanted within a patient, wherein the housing presents an upper surface, wherein the housing comprises a septum associated with the fluid reservoir, wherein the housing forms at least part of an injection port;
   (b) a septum secured to the housing, wherein the septum is configured to provide access to the reservoir, wherein the septum has an upper surface, wherein the upper surface is exposed relative to the housing;
   (c) one or more deployable protrusions associated with the housing but separate from the septum, wherein the one or more deployable protrusions are translatable along a linear path oriented about an axis perpendicular to the upper surface of the septum from a first position to a second position, wherein each protrusion presents an atraumatic tip, and wherein each tip is substantially flush with or recessed relative to an upper surface of the housing when the one or more protrusions are in the first position;
   (d) an actuator, wherein the actuator is operable to transition the one or more deployable protrusions between the first position and the second position, wherein the actuator comprises a valve;
   (e) a trigger in communication with the actuator, wherein the actuator is responsive to the trigger to transition the one or more deployable protrusions from the first position to the second position, wherein the valve of the actuator is coupled to the trigger and is configured to provide a predefined amount of fluid in response to actuation of the trigger sufficient to transition the one or more deployable protrusions between the first position and the second position;
   (f) a gastric band; and (g) a catheter in communication with the gastric band, wherein the fluid reservoir of the housing is in fluid communication with the gastric band via the catheter,
wherein the one or more deployable protrusions are at least partially retracted relative to the septum when the one or more deployable protrusions are in the first position such that in the first position, the tips of the deployable protrusions are below the upper surface of the septum,
wherein the one or more deployable protrusions are at least partially extended relative to the septum when the one or more deployable protrusions are in the second position such that in the second position, the tips of the deployable protrusions are above the upper surface of the septum, wherein at least part of the one or more deployable protrusions are positioned above the upper surface of the housing when the one or more deployable protrusions are in the second position.

2. The apparatus of claim 1, wherein the one or more deployable protrusions comprise a plurality of posts.

3. The apparatus of claim 2, wherein each of the posts has a generally cylindraceous shape.

4. The apparatus of claim 2, wherein each tip is generally blunt.

5. The apparatus of claim 4, wherein the upper tip of each post is substantially flush with or recessed relative to the upper surface of the housing when the posts are in the first position, wherein the upper tip of each post is positioned above the upper surface of the housing when the posts are in the second position.

6. The apparatus of claim 2, wherein the plurality of posts comprises four posts, wherein the four posts are substantially equidistantly spaced relative to each other.

7. The apparatus of claim 2, wherein each of the posts is operable to move along a respective linear path to transition between the first and second positions.

8. The apparatus of claim 1, wherein each of the one or more deployable protrusions has a generally arcuate shape.

9. The apparatus of claim 8, wherein each of the one or more deployable protrusions has a generally semicircular shape.

10. The apparatus of claim 1, wherein the actuator is associated with the housing.

11. The apparatus of claim 10, wherein the actuator further comprises a resilient member.

12. The apparatus of claim 11, wherein the resilient member is configured to bias the one or more deployable protrusions to the second position, wherein the actuator is operable to selectively retain the one or more deployable protrusions in the first position against the bias of the resilient member.

13. The apparatus of claim 1, wherein the trigger is responsive to a downward force exerted on the trigger, to thereby activate the actuator to transition the one or more deployable protrusions from the first position to the second position.

14. The apparatus of claim 1, wherein the trigger is responsive to a magnetic field encountered by the trigger, to thereby activate the actuator to transition the one or more deployable protrusions from the first position to the second position.

15. The apparatus of claim 1, wherein the actuator is responsive to a control signal to transition the one or more deployable protrusions from the first position to the second position.

16. The apparatus of claim 15, wherein the actuator comprises a solenoid,

17. An apparatus, comprising:
(a) a housing defining a fluid reservoir, wherein the housing is sized and configured to be implanted within a patient, wherein the housing presents an upper surface;
(b) a septum secured to the housing, wherein the septum is configured to provide access to the reservoir, wherein the septum has an upper surface, wherein the upper surface is exposed relative to the housing;
(c) one or more deployable protrusions associated with the housing, wherein the protrusions are positioned laterally outside a perimeter of the septum in a circumferentially extending array, wherein each of the one or more deployable protrusions has a blunt portion, wherein the one or more protrusions are configured to translate selectively along an axis perpendicular to the upper surface of the septum from a first position to a second position, wherein the blunt portions of the one or more protrusions are substantially flush with or recessed relative to the upper surface of the housing when the one or more protrusions are in the first position, wherein the blunt portions of the one or more protrusions are extended relative to the upper surface of the housing when the one or more protrusions are in the second position, wherein the blunt portions of the protrusions are positioned on a first side of an upper surface of the septum when in the first position, and wherein the blunt portions of the protrusions are positioned on second side of the upper surface of the septum when in the second position;
(d) an actuator, wherein the actuator is operable to move the one or more protrusions from the first position to the second position;
(e) a trigger in communication with the actuator, wherein the trigger is responsive to a downward force exerted on the trigger to activate the actuator, to thereby move the one or more protrusions from the first position to the second position;
(f) a lockout feature positioned on the housing but away from the one or more deployable protrusions, wherein the lockout feature includes one or more bosses that are configured to mechanically prevent the trigger from activating the actuator until the lockout feature has been disabled
(g) a gastric band; and
(h) a catheter in communication with the gastric band, wherein the fluid reservoir of the housing is in fluid communication with the gastric band via the catheter.

18. An apparatus, comprising:
(a) a housing defining a fluid reservoir, wherein the housing is sized and configured to be implanted within a patient, wherein the housing presents an upper surface;
(b) a septum secured to the housing, wherein the septum is configured to provide access to the reservoir, wherein the septum has an upper surface, wherein the upper surface is exposed relative to the housing;
(c) a plurality of deployable protrusions associated with the housing, wherein each of the protrusions has a blunt portion, wherein the protrusions are configured to translate selectively along an axis perpendicular to the upper surface of the septum from a first position to a second position, wherein the blunt portions of the protrusions are substantially flush with or recessed relative to the upper surface of the housing when the protrusions are in the first position, wherein the blunt portions of the protrusions are extended relative to the upper surface of the housing when the protrusions are in the second position, wherein the blunt portions of the protrusions are positioned below an upper surface of the septum when in the first position, and wherein the blunt portions of the protrusions are positioned above the upper surface of the septum when in the second position;

(d) an actuator within the housing, wherein the actuator is operable to move the protrusions from the first position to the second position, wherein the actuator is responsive to a first electrical signal to move the protrusions from the first position to the second position;

(e) a transcutaneous energy transfer coil, wherein the transcutaneous energy transfer coil is configured to provide the electrical signal to the actuator, and wherein the transcutaneous energy transfer coil is operable to receive RF energy transcutaneously from an external coil;

(f) a trigger in communication with the actuator, wherein the trigger is responsive to a downward force exerted on the trigger to activate the actuator, to thereby move the protrusions independently of the transcutaneous energy transfer coil;

(g) a lockout feature positioned on the housing but away from the deployable protrusions, wherein the lockout feature is configured to prevent the protrusions from moving to the second position until the lockout feature is disabled or the transcutaneous energy transfer coil receives RF energy;

(h) a sensor, wherein the sensor is in communication with the fluid reservoir, wherein the sensor is operable to detect changes in pressure within the fluid reservoir, wherein the sensor is configured to send a second electrical signal to the actuator in response to a change in pressure within the fluid reservoir, wherein the actuator is responsive to the second electrical signal to move the protrusions from the second position to the first position in response to the change in pressure within the fluid reservoir., (i) a gastric band; and (j) a catheter in communication with the gastric band, wherein the fluid reservoir of the housing is in fluid communication with the gastric band via the catheter.

* * * * *